(12) United States Patent
Liu et al.

(10) Patent No.: US 11,234,755 B2
(45) Date of Patent: Feb. 1, 2022

(54) ENERGY-BASED SURGICAL INSTRUMENT FOR GRASPING, TREATING, AND/OR CUTTING TISSUE

(71) Applicant: COVIDIEN LP, Mansfield, MA (US)

(72) Inventors: Kai Liu, Hunan (CN); Hongying Shi, Shanghai (CN); Xinmeng Liu, Shanghai (CN); Jiewu Cao, Shanghai (CN); Yuanxun Li, Shanghai (CN); Shaohua Wang, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 313 days.

(21) Appl. No.: 16/493,612

(22) PCT Filed: Mar. 13, 2017

(86) PCT No.: PCT/CN2017/076429
§ 371 (c)(1),
(2) Date: Sep. 12, 2019

(87) PCT Pub. No.: WO2018/165814
PCT Pub. Date: Sep. 20, 2018

(65) Prior Publication Data
US 2020/0107874 A1 Apr. 9, 2020

(51) Int. Cl.
*A61B 18/14* (2006.01)
*A61B 17/28* (2006.01)
(Continued)

(52) U.S. Cl.
CPC ...... *A61B 18/1442* (2013.01); *A61B 17/2833* (2013.01); *A61B 17/2812* (2013.01);
(Continued)

(58) Field of Classification Search
CPC ............ A61B 17/2812; A61B 17/2833; A61B 2017/2946; A61B 17/3201;
(Continued)

(56) References Cited

U.S. PATENT DOCUMENTS 5,951,549 A * 9/1999 Richardson ........ A61B 18/1445
606/45
2003/0199869 A1 10/2003 Johnson et al.
2014/0031821 A1* 1/2014 Garrison ............ A61B 17/2841
606/52

FOREIGN PATENT DOCUMENTS

CN 106063725 A 11/2016
EP 1645238 A1 4/2006
(Continued)

OTHER PUBLICATIONS

EP17901090.5, Extended European Search Report, dated Oct. 21, 2020, 5pages.
(Continued)

*Primary Examiner* — Ronald Hupczey, Jr.
*Assistant Examiner* — Bradford C. Blaise
(74) *Attorney, Agent, or Firm* — Carter, DeLuca & Farrell LLP

(57) ABSTRACT

A surgical instrument (100) includes first and second shaft members (110, 120) defining proximal and distal end portions (112*a*, 122*a*, 112*b*, 122*b*) and including handles (114, 124) at the proximal end portions (112*a*, 122*a*) thereof. A pivot member (130) couples the distal end portions (112*b*, 122*b*) with a gap (G) defined therebetween proximally of the pivot member (130). First and second jaw members (210, 220) extend distally from the shaft members (110,120), distally of the pivot member (130). A lockout bar (160, 560, 660, 760) is movable between an unlocked position, withdrawn from the gap (G), and a locked position, disposed within the gap (G). The handles (114, 124) are pivotable between spaced-apart and approximated positions to pivot the jaw members (210, 220) between open and closed positions. The handles (114, 124) are yawable between the approximated position and a yawed position to yaw the jaw members (210, 220) between the closed position and a (Continued)

cutting position. The gap (G) provides clearance to permit yawing such that, when the lockout bar (160, 560, 660, 760) is disposed in the locked position, yawing of the handles (114, 124) is inhibited.

15 Claims, 6 Drawing Sheets

(51) Int. Cl.
*A61B 18/00* (2006.01)
*A61B 17/29* (2006.01)
*A61B 17/3201* (2006.01)

(52) U.S. Cl.
CPC ... *A61B 17/3201* (2013.01); *A61B 2017/2946* (2013.01); *A61B 2018/00077* (2013.01); *A61B 2018/00601* (2013.01); *A61B 2018/00607* (2013.01); *A61B 2018/146* (2013.01); *A61B 2018/1452* (2013.01)

(58) Field of Classification Search
CPC .......... A61B 2018/00077; A61B 2018/00601; A61B 2018/00607; A61B 18/1442; A61B 18/1445; A61B 2018/146
See application file for complete search history.

(56) References Cited

FOREIGN PATENT DOCUMENTS

| | | |
|---|---|---|
| GN | 106063724 A | 11/2016 |
| WO | 20160169036 A1 | 10/2016 |
| WO | 20160169039 A1 | 10/2016 |
| WO | 20160169040 A1 | 10/2016 |
| WO | 2017031712 A1 | 3/2017 |

OTHER PUBLICATIONS

Insternational Search Report and Written Opinion issued in corresponding Appl. No. PCT/CN2017/076429 dated Dec. 25, 2017 (12 pages).

* cited by examiner

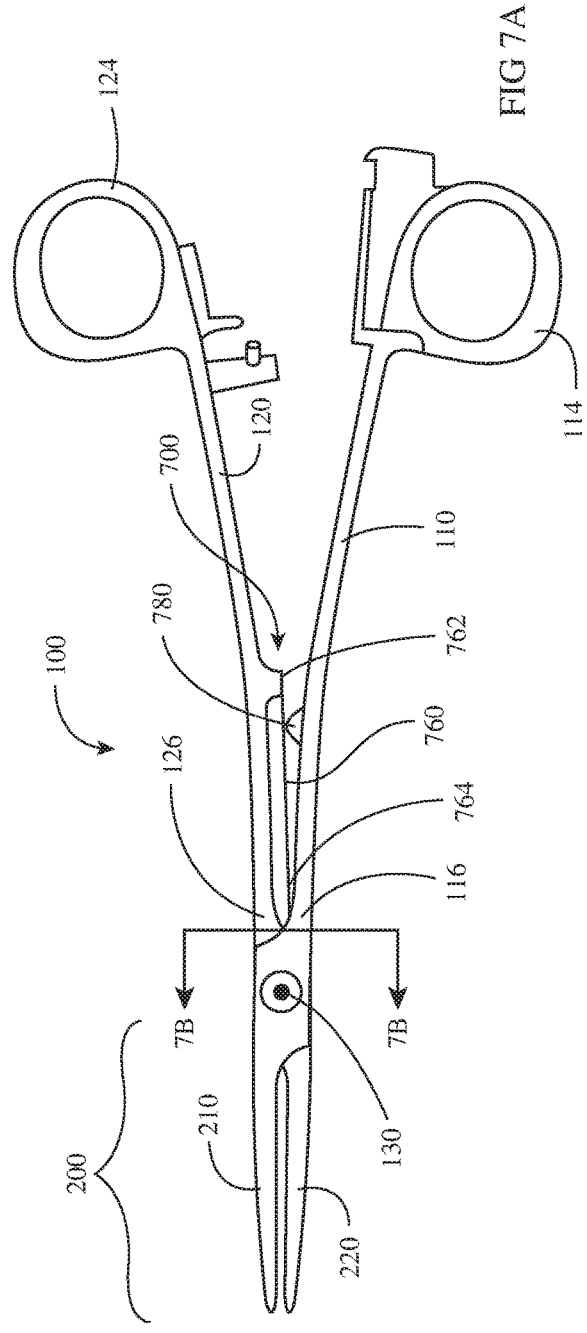
FIG 7A
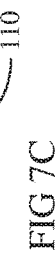
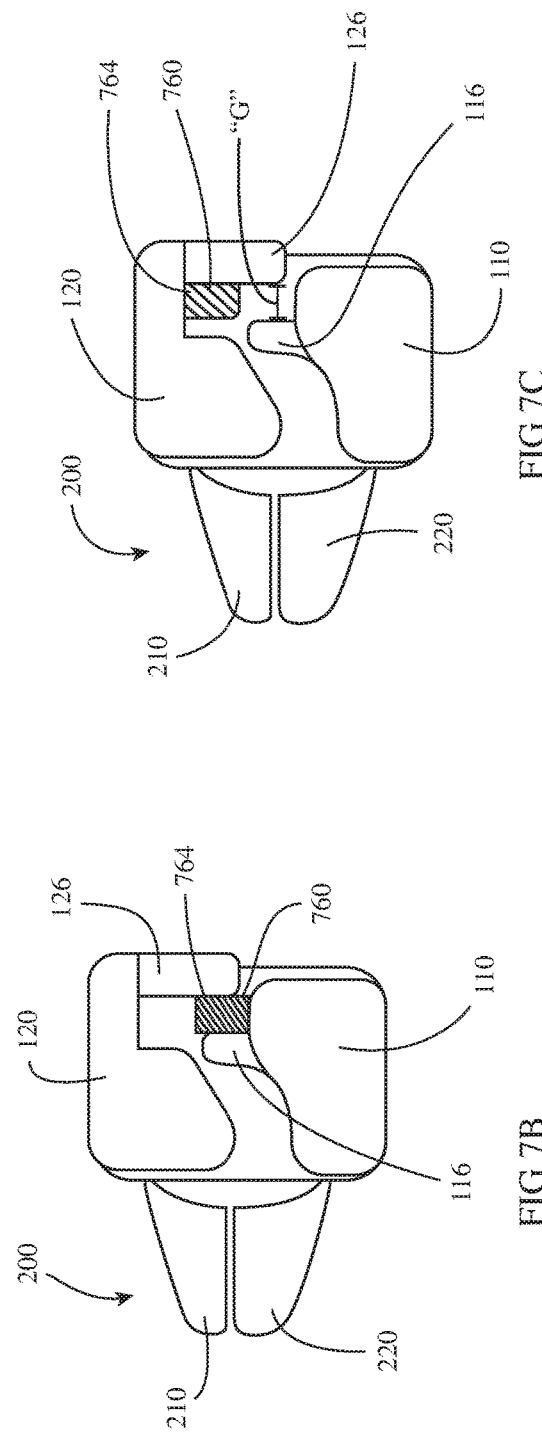
FIG 7B
FIG 7C

ENERGY-BASED SURGICAL INSTRUMENT FOR GRASPING, TREATING, AND/OR CUTTING TISSUE

BACKGROUND

1. Technical Field

The present disclosure relates to surgical instruments and, more particularly, to energy-based surgical forceps configured to grasp, treat, and/or cut tissue.

2. Background of Related Art

A forceps or hemostat is a plier-like surgical instrument which relies on mechanical action between its jaws to grasp, clamp, and constrict tissue. Energy-based forceps utilize both mechanical clamping action and energy, e.g., electrosurgical energy, ultrasonic energy, light energy, microwave energy, thermal energy, etc., to affect hemostasis by heating tissue to treat, e.g., coagulate, cauterize, and/or seal, tissue. Typically, once tissue is treated, the surgeon has to accurately sever the treated tissue. Accordingly, many energy-based forceps have been designed to incorporate a cutting mechanism that enables tissue to be cut after treatment or where only tissue cutting is desired.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A surgical instrument provided in accordance with aspects of the present disclosure includes first and second shaft members each defining a proximal end portion and a distal end portion. Each of the first and second shaft members also includes a handle disposed at the proximal end portion thereof. A pivot member defining a pivot axis pivotably couples the distal end portions of the first and second shaft members with one another. A gap is defined between the distal end portions of the first and second shaft members proximally of the pivot member.

The surgical instrument further includes first and second jaw members extending distally from the distal end portions of the respective first and second shaft members. The first and second jaw members are positioned distally of the pivot member.

A lockout bar is movable between an unlocked position, wherein the lockout bar is withdrawn from the gap, and a locked position, wherein the lockout bar is disposed within the gap.

The handles of the first and second shaft members are pivotable relative to one another in directions perpendicular to the pivot axis between a spaced-apart position and an approximated position to pivot the first and second jaw members relative to one another between an open position and a closed position. The handles of the first and second shaft members are further yawable relative to one another in directions parallel to the pivot axis between the approximated position and a yawed position to yaw the first and second jaw members relative to one another between the closed position and a cutting position. The gap provides clearance to permit yawing of the handles of the first and second shaft members such that, when the lockout bar is disposed in the locked position, yawing of the handles of the first and second shaft members is inhibited.

In an aspect of the present disclosure, the lockout bar is moved from the locked position to the unlocked position upon pivoting of the handles of the first and second shaft members from the spaced-apart position to the approximated position.

In another aspect of the present disclosure, the lockout bar is progressively moved from the locked position towards the unlocked position as the handles of the first and second shaft members are progressively moved from the spaced-apart position towards the approximated position.

In still another aspect of the present disclosure, the lockout bar is translated along one of the first or second shaft members from the locked position to the unlocked positions.

In another aspect of the present disclosure, the lockout bar is moved towards one of the shaft members and away from the other shaft member from the locked position to the unlocked position.

In yet another aspect of the present disclosure, the lockout bar is coupled to a leaf spring disposed between the first and second shaft members. In such aspects, approximation of the first and second shaft members may urge the leaf spring proximally, thereby moving the lockout bar from the locked position to the unlocked position.

In still yet another aspect of the present disclosure, the lockout bar defines a cantilever configuration engaged at a proximal end portion thereof to one of the shaft members. In such aspects, approximation of the first and second shaft members may urge a protrusion extending from the other shaft member into the lockout bar to thereby urge the lockout bar from the locked position to the unlocked position.

In another aspect of the present disclosure, the lockout bar is coupled to a rotatable member at a proximal end portion thereof. The rotatable member is rotatably coupled to one of the shaft members and configured such that rotation of the rotatable member between a first position and a second position moves the lockout bar between the locked position and the unlocked position.

In an aspect of the present disclosure, each of the first and second jaw members defines a stepped configuration including an interior corner. Yawing of the first and second jaw members from the closed position to the cutting position shears the interior corners relative to one another to cut tissue disposed therebetween. In such aspects, the interior corners may be chamfered at angles from about 70 degrees to about 80 degrees or, more particularly, at angles of about 75 degrees.

In still another aspect of the present disclosure, the handles of the first and second shaft members define finger holes and include annular ramped portions extending about a portion of the circumference of the finger holes. The annular ramped portions are configured to facilitate yawing of the handles of the first and second shaft members.

In another aspect of the present disclosure, at least one of the jaw members is adapted to connect to a source of energy for treating tissue grasped between the first and second jaw members. In such aspects, the lockout bar is moved from the locked position to the unlocked position upon initiation of the supply of energy to the jaw member(s).

BRIEF DESCRIPTION OF THE DRAWINGS

Various aspects and features of the present disclosure are described hereinbelow with reference to the drawings wherein like numerals designate identical or corresponding elements in each of the several views and:

FIG. 7A is a side view of the forceps of FIG. 1 including yet another lockout mechanism provided in accordance with the present disclosure, with the attachment member thereof removed;

FIG. 7B is a transverse, cross-sectional view of the forceps of FIG. 7A taken across section line 7B-7B of FIG. 7A, wherein a lockout bar of the lockout mechanism is disposed in a locked position;

FIG. 7C is a transverse, cross-sectional view of the forceps of FIG. 7A, wherein the lockout bar is disposed in an unlocked position.

DETAILED DESCRIPTION

Figure 1:
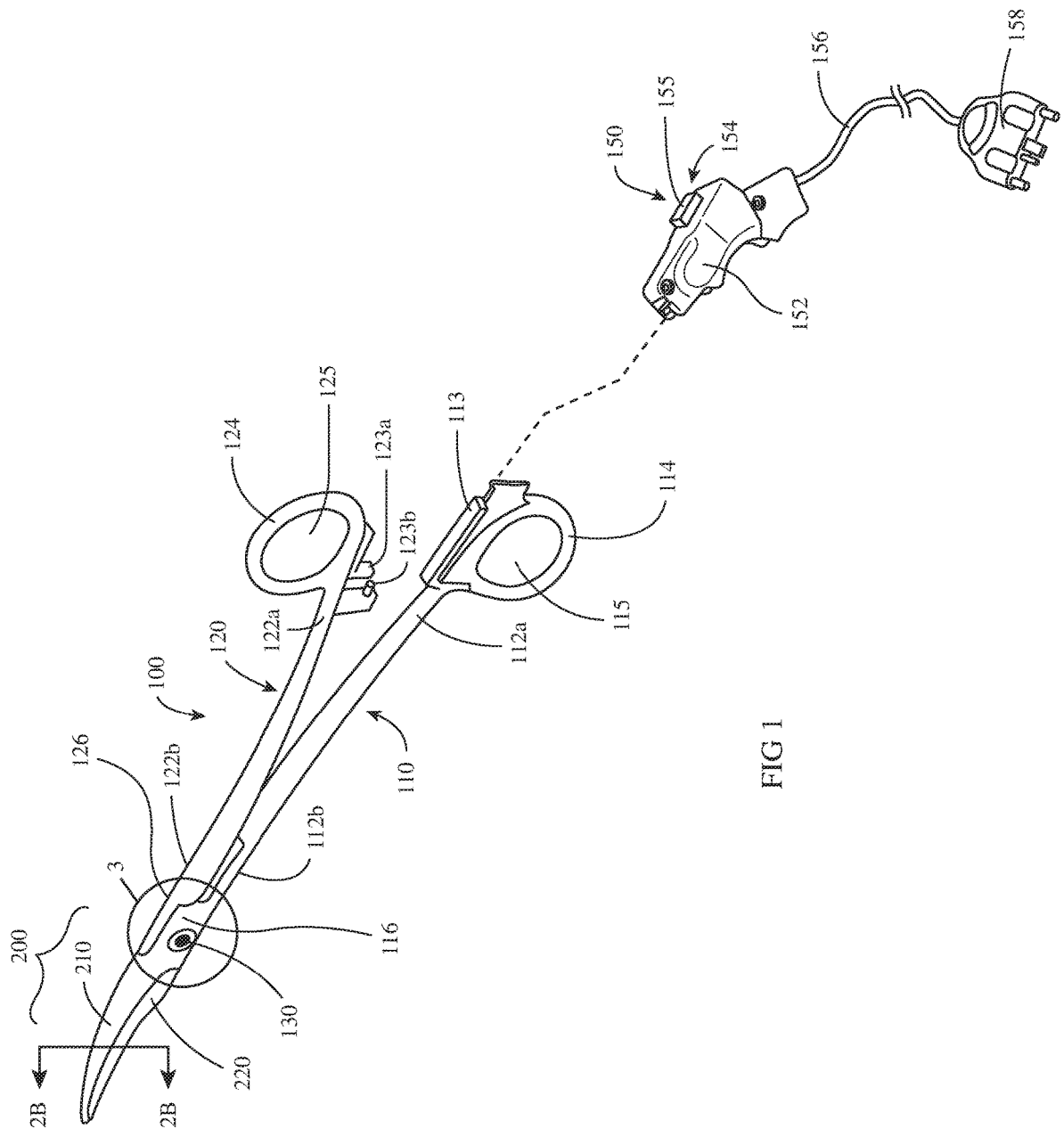
FIG. 1 is a rear, perspective view of an energy-based surgical forceps provided in accordance with the present disclosure, with an attachment member thereof separated therefrom.

Referring now to FIG. 1, an energy-based surgical forceps 100 provided in accordance with the present disclosure includes first and second shaft members 110, 120 each having a proximal end portion 112a, 122a and a distal end portion 112b, 122b, respectively. An end effector assembly 200 of forceps 100 includes first and second jaw members 210, 220 extending from distal end portions 112b, 122b of shaft members 110, 120, respectively. Forceps 100 further includes a pivot member 130 pivotably coupling first and second shaft members 110, 120 with one another, and an attachment member 150 releasably engagable with the proximal end portion of one of the shaft members, e.g., proximal end portion 112a of shaft member 110. Alternatively, attachment member 150 may be permanently affixed to the corresponding shaft member, e.g., proximal end portion 112a of shaft member 110.

Shaft members 110, 120 are formed at least partially from an electrically-conductive material such that electrosurgical energy may be transmitted therealong to and from jaw members 210, 220, respectively. Alternatively, shaft members 110, 120 may house conductors (not shown) configured to transmit electrosurgical energy to and from jaw members 210, 220. Proximal end portions 112a, 122a of shaft members 110, 120, respectively, include handles 114, 124 defining finger holes 115, 125 configured to facilitate grasping and manipulating shaft members 110, 120. Proximal end portion 112a of shaft member 110 further includes an engagement sled 113 configured to facilitate sliding of attachment member 150 onto and into engagement about proximal end portion 112a of shaft member 110. Proximal end portion 122a of shaft member 120, on the other hand, includes an activation finger 123a and an electrical connection pin 123b, the functions of which are detailed below.

Figure 2:
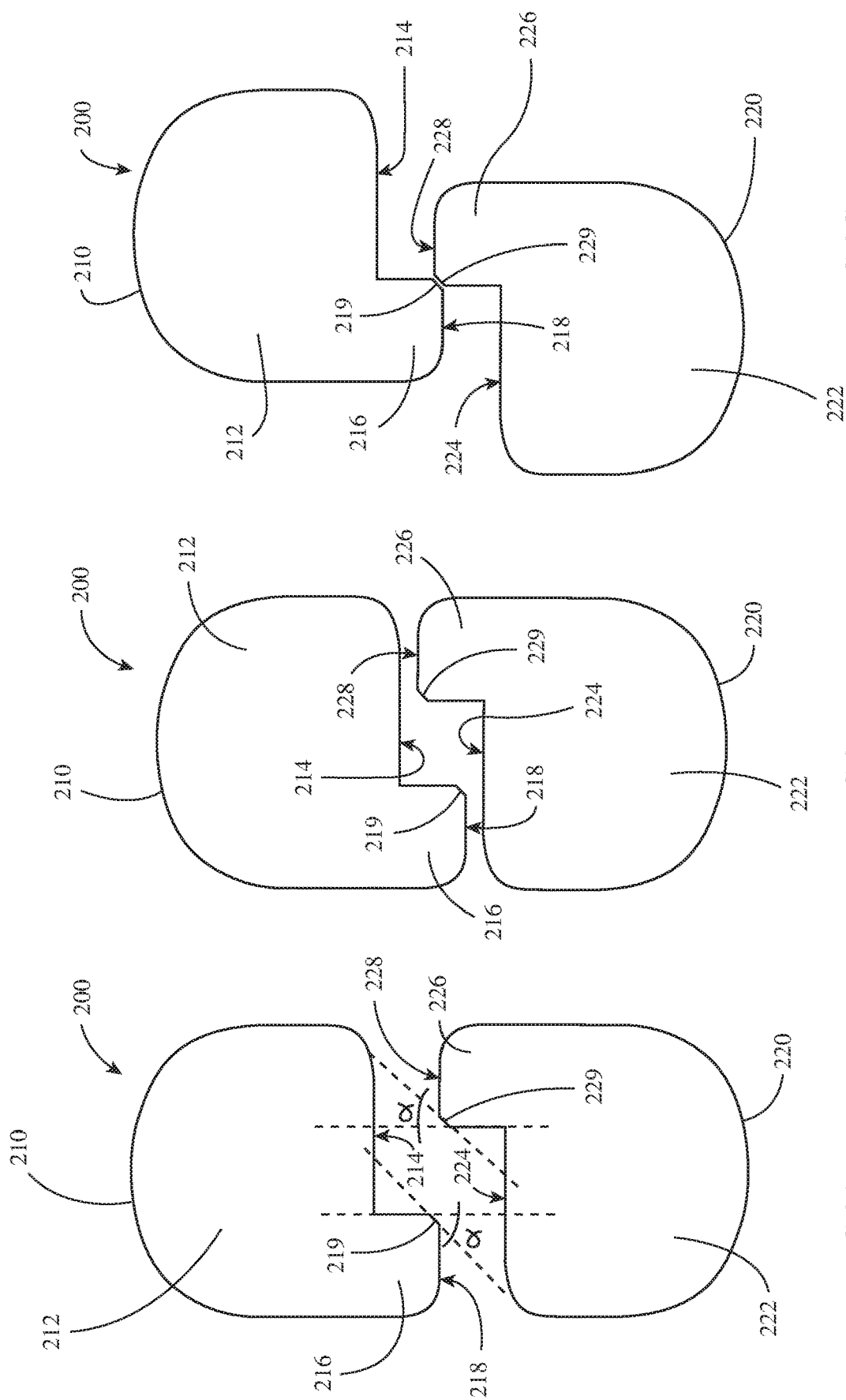
FIG. 2A is a transverse, cross-sectional view of jaw members of the forceps of FIG. 1, disposed in an open position.
FIG. 2B is a transverse, cross-sectional view taken across section line 2B-2B of FIG. 1, wherein the jaw members are disposed in a closed position.
FIG. 2C is a transverse, cross-sectional view of the jaw members of the forceps of FIG. 1, disposed in a cutting position.

Distal end portions 112b, 122b of shaft members 110, 120 form uprights 116, 126 (see also FIG. 3) defining aligned pivot apertures 117, 127 configured to receive pivot member 130 therethrough for pivotably coupling distal end portions 112b, 122b of shaft members 110, 120 with one another. As a result of this configuration, handles 114, 124 are movable relative to one another in directions substantially perpendicular to a pivot axis of pivot member 130, e.g., vertically given the orientation of forceps 100 in FIG. 1, between a spaced-apart position and an approximated position to pivot jaw members 210, 220 about pivot member 130 and relative to one another between an open position (FIG. 2A) and a closed position (FIG. 2B).

Figure 3:
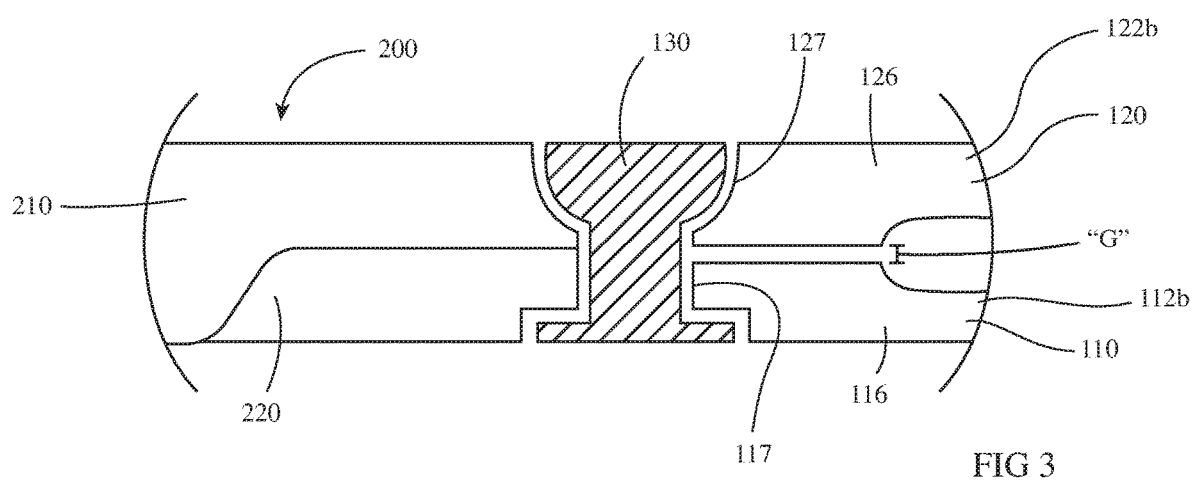
FIG. 3 is a top, longitudinal, cross-sectional view of the area indicated as "3" in FIG. 1.

With momentary reference to FIG. 3, uprights 116, 126 of distal end portions 112b, 122b of shaft members 110, 120, respectively, define a gap "G" therebetween proximally of pivot member 130. This gap "G" permits handles 114, 124 to be further movable relative to one another in directions substantially parallel to the pivot axis of pivot member 130, e.g., horizontally given the orientation of forceps 100 in FIG. 1, between the approximated position, wherein jaw members 210, 220 are disposed in the closed position (FIG. 2B), to a yawed position, wherein jaw members 210, 220 are disposed in a cutting position (FIG. 2C).

Referring again to FIG. 1, attachment member 150 includes a housing 152 configured for slidable positioning about and releasable engagement with proximal end portion 112a of shaft member 110, a switch assembly 154 disposed within housing 152 and including an activation button 155 extending therefrom, an electrosurgical cable 156 extending proximally from housing 152, a plug 158 disposed at the free proximal end portion of electrosurgical cable 156 to enable connection of attachment member 150 to a source of energy (not shown), e.g., an electrosurgical generator, a plurality of electrical lead wires (not shown) extending through electrosurgical cable 156 and into housing 152, and first and second electrical contacts (not shown) disposed within housing 152. The first electrical contact (not shown) is disposed in electrical communication with shaft member 110 to establish electrical communication between one or more of the plurality of electrical lead wires (not shown) and first jaw member 210, while the second electrical contact (not shown) is positioned such that, in the first approximated position of handles 114, 124 of shaft members 110, 120, respectively, electrical connection pin 123b contacts the second electrical contact (not shown) to establish electrical communication between one or more of the plurality of electrical lead wires (not shown) and second jaw member 220. However, other suitable electrical connection arrangements are also contemplated.

Switch assembly 154 of attachment member 150 is positioned such that, upon movement of handles 114, 124 of shaft members 110, 120, respectively, to the approximated position, activation finger 123*a* of proximal end portion 122*a* of shaft member 120 is sufficiently urged into contact with activation button 155 to actuate activation button 155. One of more of the plurality of electrical lead wires (not shown) of attachment member 150 is coupled to activation button 155, thus enabling initiation of the supply of electrosurgical energy to jaw members 210, 220 of end effector assembly 200 upon actuation of activation button 155 of switch assembly 154, e.g., for treating tissue grasped between jaw members 210, 220.

With additional reference to FIGS. 2A-2C, end effector assembly 200, as mentioned above, includes first and second jaw members 210, 220 pivotable relative to one another between the open position (FIG. 2A), the closed position (FIG. 2B), and the cutting position (FIG. 2C). Each jaw member 210, 220 includes a body 212, 222 defining a first tissue-contacting surface 214, 224 and a step 216, 226 extending from the respective body 212, 222 towards the other jaw members 210, 220 and defining a second tissue-contact surface 218, 228, respectively. Steps 216, 226 of jaw members 210, 220 are laterally offset relative to one another such that, in an aligned orientation of jaw members 210, 220, second tissue-contact surface 218 of jaw member 210 opposes a portion of first tissue-contacting surface 224 of jaw member 220 and such that second tissue-contact surface 228 of jaw member 220 opposes a portion of first tissue-contacting surface 214 of jaw member 210. Further, first tissue-contacting surfaces 214, 224 define greater widths as compared to second tissue-contacting surfaces 218, 228 such that the portions of first tissue-contacting surfaces 214, 224 extending between steps 216, 226 also oppose one another.

With reference to FIG. 2A, in the open position of jaw members 210, 220, jaw members 210, 220 are spaced-apart from one another and disposed in the aligned orientation relative to one another, wherein second tissue-contact surface 218 of jaw member 210 opposes a portion of first tissue-contacting surface 224 of jaw member 220, second tissue-contact surface 228 of jaw member 220 opposes a portion of first tissue-contacting surface 214 of jaw member 210, and the portions of first tissue-contacting surfaces 214, 224 extending between steps 216, 226 also oppose one another.

Referring to FIG. 2B, in the closed position of jaw members 210, 220, jaw members 210, 220 are approximated relative to one another but maintained in the aligned orientation. More specifically, second tissue-contact surface 218 of jaw member 210 is approximated relative to the opposing portion of first tissue-contacting surface 224 of jaw member 220 and second tissue-contact surface 228 of jaw member 220 is approximated relative to the opposing portion of first tissue-contacting surface 214 of jaw member 210. The opposing portions of first tissue-contacting surfaces 214, 224 extending between steps 216, 226 are closer to one another than in the open position (FIG. 2A) but remain spaced due to steps 216, 226. One or more stop members (not shown) or other suitable features may be provided to maintain a minimum distance between second tissue-contact surface 218 of jaw member 210 and the opposing portion of first tissue-contacting surface 224 of jaw member 220 and between second tissue-contact surface 228 of jaw member 220 and the opposing portion of first tissue-contacting surface 214 of jaw member 210 in the closed position.

Movement of jaw members 210, 220 between the open and closed positions (FIGS. 2A and 2B, respectively), may be effectuated in order to grasp and/or manipulate tissue. With tissue grasped between jaw members 210, 220 in the closed position thereof, electrosurgical energy may be conducted between jaw members 210, 220 to treat tissue grasped therebetween, e.g., upon actuation of activation button 155 (FIG. 1). More specifically, electrosurgical energy is conducted between second tissue-contact surface 218 of jaw member 210 and the opposing portion of first tissue-contacting surface 224 of jaw member 220 to treat, e.g., seal, tissue therebetween, and between second tissue-contact surface 228 of jaw member 220 and the opposing portion of first tissue-contacting surface 214 of jaw member 210 to treat, e.g., seal, tissue therebetween. Electrosurgical energy may also be conducted transversely across the portions of first tissue-contacting surfaces 214, 224 extending between steps 216, 226 to treat, e.g., seal, tissue disposed therebetween.

With reference to FIG. 2C, in the cutting position of jaw members 210, 220, jaw members 210, 220 are offset relative to one another such that movement of jaw members 210, 220 from the closed position to the cutting positions results in shearing action between the interior corners 219, 229 of steps 216, 226 to cut tissue disposed therebetween. Rather than being squared off, it has been found that providing chamfered interior corners 219, 229 promotes consistent, effective tissue cutting. Further, chamfered interior corners 219, 229 reduce wearing, thus ensuring effective and reliable tissue cutting, particularly in embodiments where at least a portion of surgical forceps 100 (FIG. 1) is configured as a sterilizable, reusable device. In such reusable embodiments, attachment member 150 (FIG. 1) may be a single-use, disposable component or may also be sterilizable and reusable.

Referring also to FIG. 2A, the angle (a) of chamfered interior corners 219, 229 may, in embodiments, be from about 70° to about 80°; in other embodiments, from about 72° to about 78°; in still other embodiments, from about 74° to about 76°; and, in yet other embodiments, about 75°.

Turning to FIG. 3, as noted above, uprights 116, 126 of distal end portions 112*b*, 122*b* of shaft members 110, 120, respectively, define gap "G" therebetween which is proximal of pivot member 130 to enable handles 114, 124 (FIG. 1) to move between the approximated position, wherein jaw members 210, 220 are disposed in the closed position (FIG. 2B), and the yawed position, wherein jaw members 210, 220 are disposed in the cutting position (FIG. 2C). More specifically, as handles 114, 124 (FIG. 1) are moved from the approximated position to the yawed position, uprights 116, 126, disposed proximally of pivot member 130, are moved towards one another, eliminating or reducing gap "G," while jaw members 210, 220, disposed distally of pivot member 130, are correspondingly moved laterally apart from one another from the closed position (FIG. 2B) to the cutting position (FIG. 2C). Thus, gap "G" provides suitable clearance to enable yawing of handles 114, 124 (FIG. 1) and, thus, movement of jaw members 210, 220 from the closed position (FIG. 2B) to the cutting position (FIG. 2C).

Figure 4A:
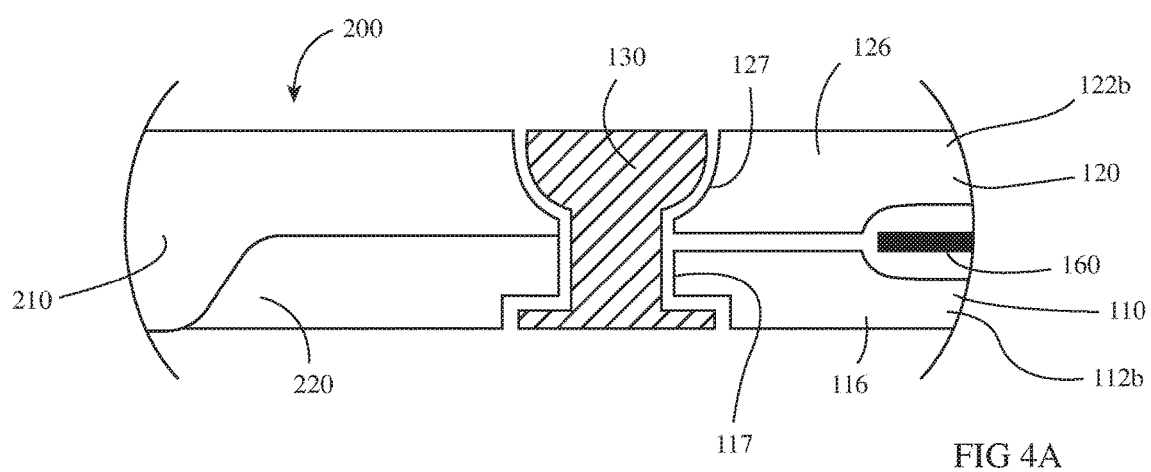
FIG. 4A is a top, longitudinal cross-sectional view of the portion of the forceps of FIG. 1 illustrated in FIG. 3, wherein a lockout bar of the forceps is disposed in an unlocked position.
Figure 4B:
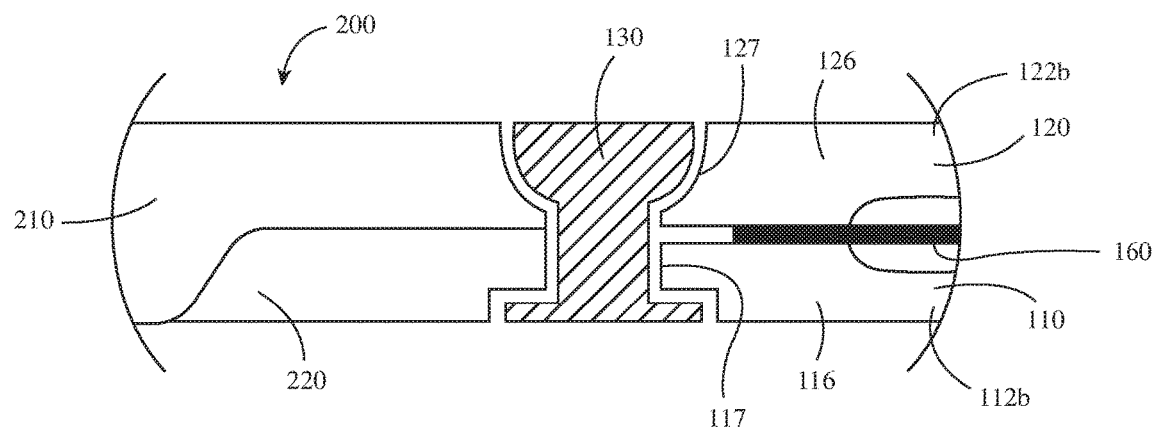
FIG. 4B is a top, longitudinal cross-sectional view of the portion of the forceps of FIG. 1 illustrated in FIG. 3, wherein the lockout bar is disposed in a locked position.

Referring to FIGS. 4A and 4B, in conjunction with FIG. 3, in embodiments, forceps 100 includes a lockout bar 160 movable into and out of the gap "G" defined between uprights 116, 126 of shaft members 110, 120. More specifically, lockout bar 160 is movable between an unlocked position (FIG. 4A), wherein lockout bar 160 is removed from gap "G" between uprights 116, 126 to enable yawing of handles 114, 124 (FIG. 1) and, thus, movement of jaw members 210, 220 from the closed position (FIG. 2B) to the cutting position (FIG. 2C), and a locked position (FIG. 4B), wherein lockout bar 160 extends between uprights 116, 126 and acts as a shim therebetween to eliminate or reduce the gap "G" such that handles 114, 124 (FIG. 1) are inhibited from yawing, thereby inhibiting movement of jaw members 210, 220 from the closed position (FIG. 2B) to the cutting position (FIG. 2C). Various embodiments of lockout bars and mechanisms for moving the same between the unlocked and locked positions are detailed below with reference to FIGS. 5, 6, and 7A-7C.

Figure 5:
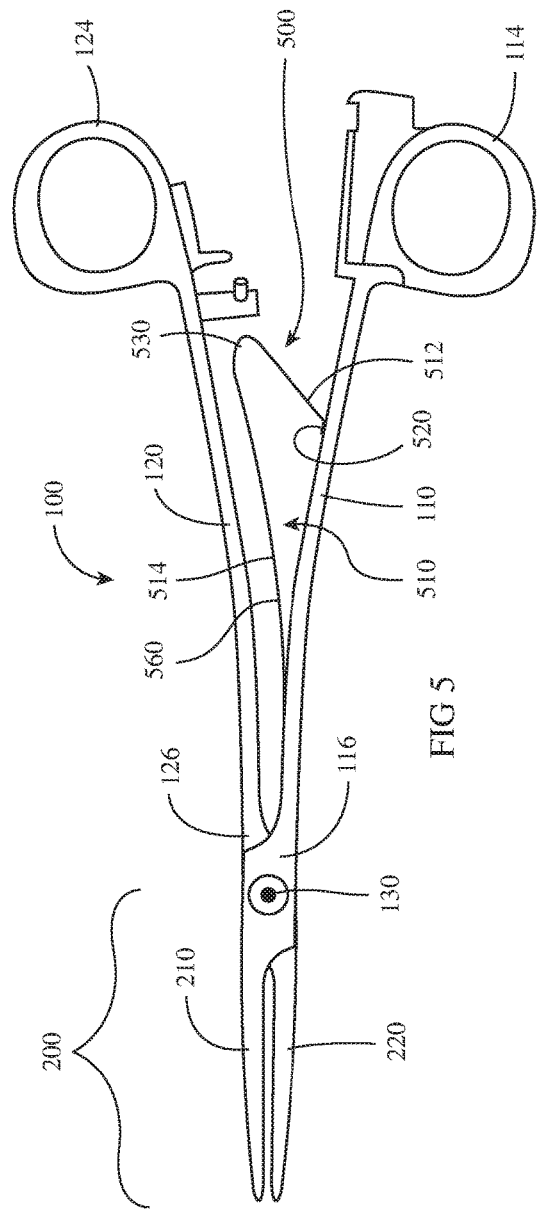
FIG. 5 is a side view of the forceps of FIG. 1 including a lockout mechanism provided in accordance with the present disclosure, and the attachment member thereof removed.

As illustrated in FIG. 5, in embodiments, a lockout mechanism 500 is providing for use with forceps 100 that includes a lockout bar 560 formed as a distal extension of a leaf spring 510. Leaf spring 510, more specifically, includes a proximal foot 520 at the proximal end portion 512 thereof, a bend 530 towards proximal end portion 512, and an elongated distal end portion 514 from which lockout bar 560 extends distally. Proximal foot 520 is engaged with shaft member 110 of forceps 100. Leaf spring 510 extends from proximal foot 520 towards shaft member 120 of forceps 100 such that bend 530 is positioned adjacent shaft member 120. Elongated distal end portion 514 and lockout bar 560 extend distally from bend 530 between shaft members 110, 120 of forceps 100. Leaf spring 510 of lockout mechanism 500 is biased towards a locked condition, corresponding to a locked position of lockout bar 560, wherein the free distal end of lockout bar 560 extends between uprights 116, 126 of shaft members 110, 120 to inhibit handles 114, 124 from yawing, thereby inhibiting movement of jaw members 210, 220 from the closed position (FIG. 2B) to the cutting position (FIG. 2C) (see also FIG. 4B).

Prior to reaching the approximated position of handles 114, 124, e.g., in the spaced-apart position of handles 114, 124 or positions between the spaced-apart and approximated positions, leaf spring 510 of lockout mechanism 500 is maintained in the locked condition, wherein the free distal end of lockout bar 560 extends between uprights 116, 126 of shaft members 110, 120. As handles 114, 124 approach the approximated position, shaft member 120 is urged into leaf spring 510 such that bend 530 of leaf spring 510 is pushed proximally, thus pulling the free distal end of lockout bar 560 proximally. However, until the approximated position is reached, the free distal end of lockout bar 560 remains disposed between uprights 116, 126 of shaft members 110, 120, thus maintaining the locked condition of lockout mechanism 500. As such, in the locked condition of lockout mechanism 500, the user may grasp tissue, effect blunt dissection of tissue, and/or otherwise manipulate tissue without applying energy thereto and without cutting tissue.

With additional reference to FIGS. 1 and 2A-2C, when it is desired to treat and/or cut tissue, handles 114, 124 may be further moved to the approximated position, wherein an appropriate pressure is applied to tissue grasped between jaw members 210, 220 and/or wherein an appropriate minimum distance between second tissue-contact surface 218 of jaw member 210 and the opposing portion of first tissue-contacting surface 224 of jaw member 220 and between second tissue-contact surface 228 of jaw member 220 and the opposing portion of first tissue-contacting surface 214 of jaw member 210 is maintained. Upon movement of handles 114, 124 to the approximated position or an actuated position beyond the approximated position (while maintaining the appropriate pressure and/or appropriate minimum distance due to flexion of shaft members 110, 120), activation finger 123a of proximal end portion 122a of shaft member 120 is sufficiently urged into contact with activation button 155 to actuate activation button 155 and initiate the supply of electrosurgical energy to jaw members 210, 220 to treat tissue grasped therebetween.

Upon reaching the approximated position, shaft member 120 is urged further into leaf spring 510 such that bend 530 of leaf spring 510 is pushed further proximally, thus pulling the free distal end of lockout bar 560 proximally to the unlocked position, wherein the free distal end of lockout bar 560 is withdrawn from between uprights 116, 126 of shaft members 110, 120, corresponding to the unlocked condition of lockout mechanism 500. In the unlocked condition, the gap "G" is defined between uprights 116, 126, thus enabling yawing of handles 114, 124 (see FIG. 3). As such, only after tissue has been treated (in embodiments where activation button 155 is actuated in the approximated positions of handles 114, 124) or where handles 114, 124 are moved to the approximated position just prior to initiation of tissue treatment (in embodiments where activation button 155 is actuated in the actuated position of handles 114, 124) is lockout mechanism 500 unlocked to enable tissue cutting.

With lockout mechanism 500 unlocked, as noted above, tissue cutting may be effected by moving handles 114, 124 to the yawed position, such that jaw members 210, 220 are moved to the cutting position, wherein interior corners 219, 229 of steps 216, 226 shear past one another to cut tissue disposed therebetween (see FIG. 2C). Forceps 100 may further be configured such that handles 114, 124 are biased towards an aligned orientation relative to one another. As such, once tissue is cut and the yawing force on handles 114, 124 removed, handles 114, 124 return to the approximated position, thus returning jaw members 210, 220 to the closed position.

Figure 6:
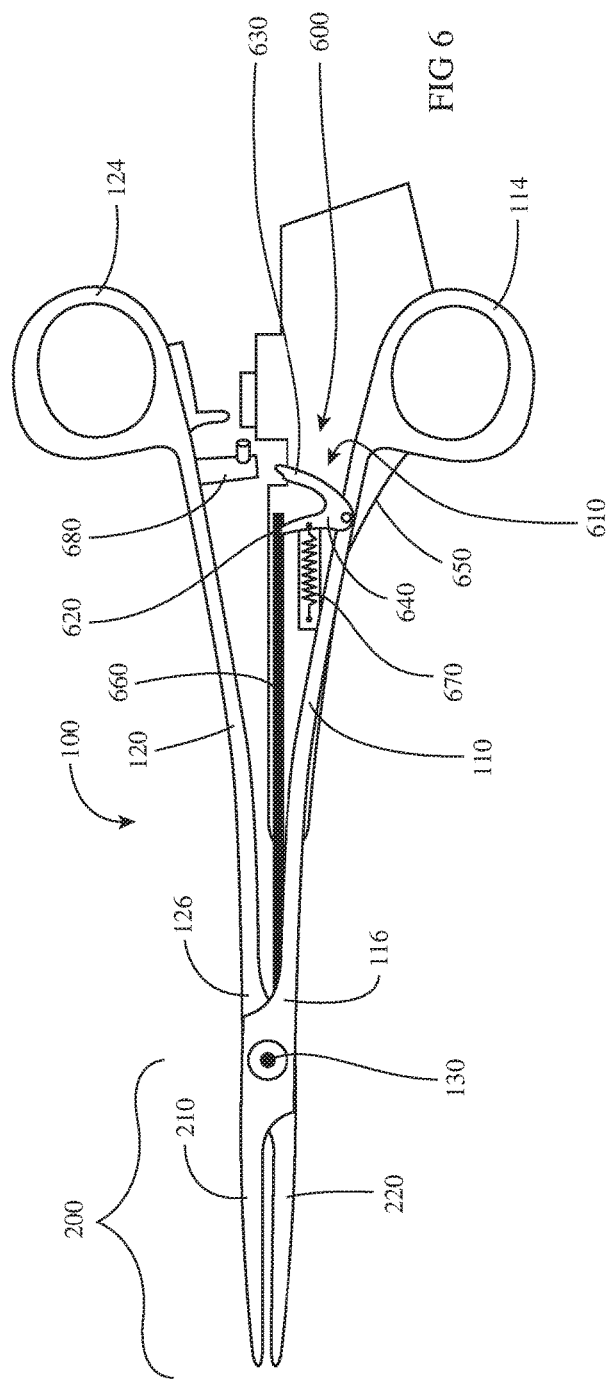
FIG. 6 is a side, partial cut-away view of the forceps of FIG. 1 including another lockout mechanism provided in accordance with the present disclosure.
Figure 8A:
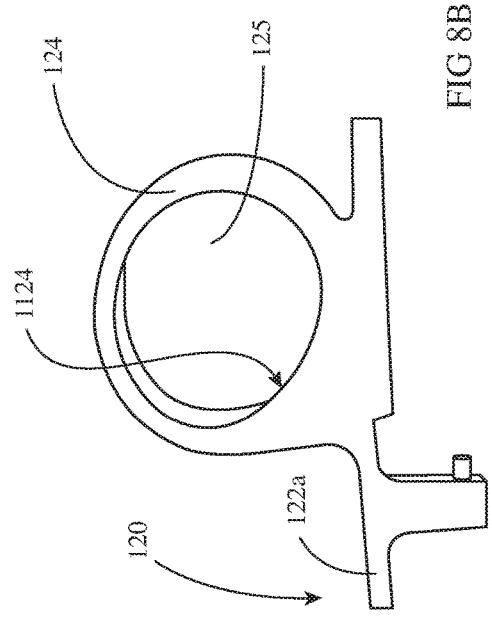
FIG. 8A-8D are perspective views, from either side thereof, of first and second handles of the forceps of FIG. 1 including yaw-facilitating features in accordance with the present disclosure.
Figure 8B:
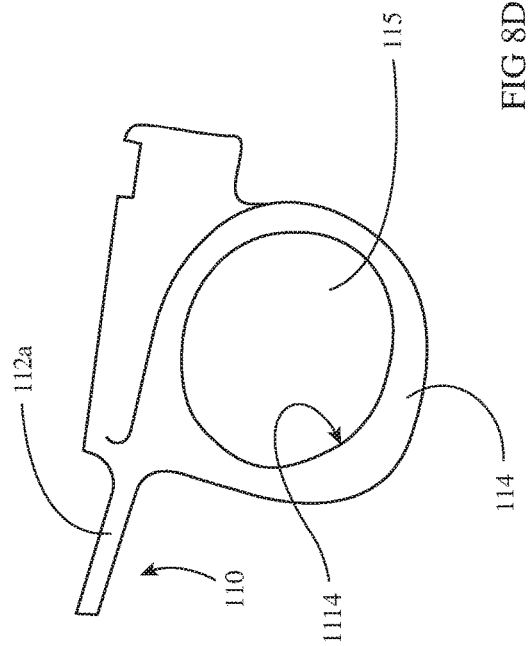
Figure 8C:
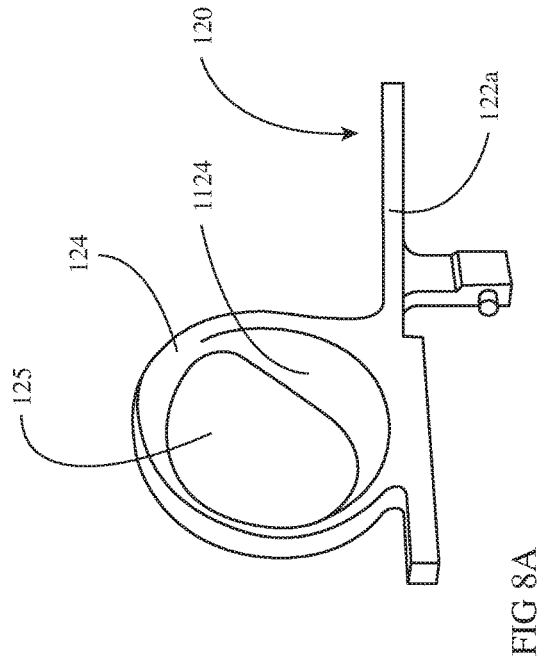
Figure 8D:
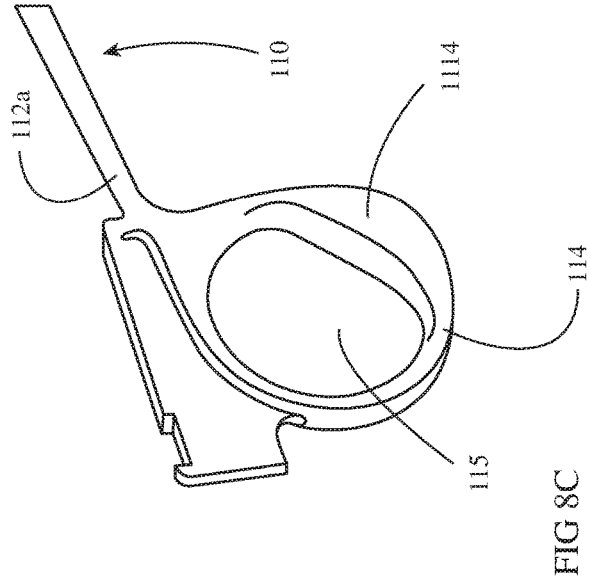

Turning to FIG. 6, another lockout mechanism 600 providing for use with forceps 100 includes a rotating member, e.g., a wishbone 610. Wishbone 610 defines a first leg 620, a second leg 630, and an apex portion 640. Locking mechanism 600 further includes a housing 650, a lockout bar 660, and a biasing spring 670. Housing 650 houses biasing spring 670, a portion of wishbone 610, and a portion of lockout bar 660. Housing 650 may be an extension of housing 152 of attachment member 150 (which, in such embodiments, may incorporate at least some components of lockout mechanism 600 therein), or may be separate therefrom.

Apex portion 640 of wishbone 610 is coupled to shaft member 110 of forceps 100, the free end of first leg 620 of wishbone 610 is coupled to a proximal end portion of lockout bar 660, and one end of biasing spring 670 is coupled to first leg 620 of wishbone 610 between the free end thereof and apex portion 640. The other end of biasing spring 670 is coupled to housing 650 distally of wishbone 610. Biasing spring 670 is configured as an extension spring and serves to bias first leg 620 of wishbone 610 distally, thus biasing lockout bar 660 distally to the locked position corresponding to the locked condition of lockout mechanism 600 (see also FIG. 4B).

The free end of second leg 630 of wishbone 610 extends from housing 650 towards handle 124 of shaft member 120. More specifically, second leg 630 of wishbone 610 is positioned such that, upon movement of handles 114, 124 to the approximated position or the actuated position, a protrusion 680 extending from handle 124 contacts the free end of second leg 630 and urges second leg 630 proximally. Proximal urging of second leg 630, in turn, urges wishbone 610 to rotate proximally against the bias of biasing spring 670, thereby pulling first leg 620 of wishbone 610 and lockout bar 660 proximally to the unlocked position. Lockout bar 660, more specifically, is pulled proximally such that the free distal end of lockout bar 660 is withdrawn from between uprights 116, 126 of shaft members 110, 120, corresponding to the unlocked condition of lockout mechanism 600. In the unlocked condition, the gap "G" is defined between uprights 116, 126, thus enabling yawing of handles 114, 124 (see FIG. 3).

Similarly as with lockout mechanism 500 (FIG. 5), lockout mechanism 600 enables tissue cutting only after tissue has been treated or where handles 114, 124 are moved to the approximated position just prior to initiation of tissue treatment. With lockout mechanism 600 unlocked, as noted above, tissue cutting may be effected by moving handles 114, 124 to the yawed position, similarly as detailed above. Once tissue cutting is complete and handles 114, 124 released, biasing spring 670 returns lockout mechanism 600 to the locked condition.

Turning to FIGS. 7A-7C, another lockout mechanism 700 is shown for use with forceps 100 and includes a lockout bar 760 defining a cantilever configuration wherein the proximal end portion 762 of lockout bar 760 is engaged to shaft member 120 of forceps 100 and wherein lockout bar 760 defines a free distal end portion 764. Lockout mechanism 700 further includes a protrusion 780 extending from shaft member 110 of forceps 100 towards shaft member 120 thereof.

Lockout bar 760 is biased towards the locked position, wherein, as shown in FIG. 7B, free distal end portion 764 of lockout bar 760 is disposed within the gap "G" (FIG. 7C) defined between uprights 116, 126 of shaft members 110, 120 of forceps 100. With free distal end portion 764 of lockout bar 760 disposed within the gap "G" (FIG. 7C), yawing of handles 114, 124 is inhibited and, thus, movement of jaw members 210, 220 to the cutting position is likewise inhibited, similarly as detailed above.

Upon movement of handles 114, 124 to the approximated position or the actuated position, protrusion 780 contacts lockout bar 760 between the proximal and distal end portions 762, 764, respectively, thereof, and urges the free distal end portion 764 towards shaft member 120. In this manner, free distal end portion 764 of lockout bar 760 is moved to the unlocked position, wherein free distal end portion 764 is withdrawn (towards shaft member 120), from the gap "G" defined between uprights 116, 126 of shaft members 110, 120, corresponding to the unlocked condition of lockout mechanism 700. In the unlocked condition, the gap "G" is defined between uprights 116, 126, thus enabling yawing of handles 114, 124 (see FIG. 3).

Similarly as with lockout mechanism 500 (FIG. 5), lockout mechanism 700 enables tissue cutting only after tissue has been treated or where handles 114, 124 are moved to the approximated position just prior to initiation of tissue treatment. With lockout mechanism 700 unlocked, tissue cutting may be effected by moving handles 114, 124 to the yawed position, similarly as detailed above. Once tissue cutting is complete and handles 114, 124 are returned towards the spaced-apart position, the bias of lockout bar 760 returns lockout bar 760 to the locked position, corresponding to the locked condition of lockout mechanism 700.

Turning to FIGS. 8A-8D, in conjunction with FIG. 1, as noted above, proximal end portions 112a, 122a of shaft members 110, 120, respectively, include handles 114, 124 defining finger holes 115, 125 configured to facilitate grasping and manipulating shaft members 110, 120. As also detailed above, handles 114, 124 are configured to yaw relative to one another, in directions substantially parallel to the pivot axis of pivot member 130, between the approximated position, wherein jaw members 210, 220 are disposed in the closed position (FIG. 2B), and the yawed position, wherein jaw members 210, 220 are disposed in a cutting position (FIG. 2C). In order to facilitate this yawing of handles 114, 124 and provide a more ergonomic feel, handles 114, 124, as detailed below, may include asymmetric features that provide increased surface area into which the surgeon's fingers may be urged to yaw handles 114, 124.

More specifically, handles 114, 124 may include annular ramp portions 1114, 1124 extending about a portion of the circumference of finger holes 115, 125 and positioned at the pressure point locations where the surgeon's finger, which extend through finger holes 115, 125, would apply pressure to handles 114, 124 to effect yawing of handles 114, 124. Annular ramp portions 1114, 1124 define areas of increased surface area to spread out the applied force and are angled to provide an opposing surface against which the surgeon's fingers are urged, thus enabling more ergonomic yawing and facilitating yawing.

While several embodiments of the disclosure have been shown in the drawings and described herein, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. A surgical instrument comprising:
   first and second shaft members, each defining a proximal end portion and a distal end portion, wherein each of the first and second shaft members includes a handle disposed at the proximal end portion thereof;
   a pivot member defining a pivot axis, the pivot member pivotably coupling the distal end portions of the first and second shaft members, wherein a gap is defined between the distal end portions of the first and second shaft members proximally of the pivot member;
   first and second jaw members extending distally from the distal end portions of the respective first and second shaft members, the first and second jaw members positioned distally of the pivot member; and
   a lockout bar movable between an unlocked position, wherein the lockout bar is withdrawn from the gap, and a locked position, wherein the lockout bar is disposed within the gap,
   wherein the handles of the first and second shaft members are pivotable relative to one another in directions perpendicular to the pivot axis between a spaced-apart position and an approximated position to pivot the first and second jaw members relative to one another between an open position and a closed position,
   wherein the handles of the first and second shaft members are yawable relative to one another in directions parallel to the pivot axis between the approximated position and a yawed position to yaw the first and second jaw members relative to one another between the closed position and a cutting position, and
   wherein, the gap provides clearance to permit yawing of the handles of the first and second shaft members such that, when the lockout bar is disposed in the locked position, yawing of the handles of the first and second shaft members is inhibited.

2. The surgical instrument according to claim 1, wherein the lockout bar is moved from the locked position to the unlocked position upon pivoting of the handles of the first and second shaft members from the spaced-apart position to the approximated position.

3. The surgical instrument according to claim 1, wherein the lockout bar is progressively moved from the locked position towards the unlocked position as the handles of the first and second shaft members are progressively moved from the spaced-apart position towards the approximated position.

4. The surgical instrument according to claim 1, wherein the lockout bar is translated along one of the first or second shaft members from the locked position to the unlocked positions.

5. The surgical instrument according to claim 1, wherein the lockout bar is moved towards one of the first or second shaft members and away from the other of the first or second shaft members from the locked position to the unlocked position.

6. The surgical instrument according to claim 1, wherein the lockout bar is coupled to a leaf spring disposed between the first and second shaft members.

7. The surgical instrument according to claim 6, wherein approximation of the first and second shaft members urges the leaf spring proximally, thereby moving the lockout bar from the locked position to the unlocked position.

8. The surgical instrument according to claim 1, wherein the lockout bar defines a cantilever configuration engaged at a proximal end portion thereof to one of the first or second shaft members.

9. The surgical instrument according to claim 8, wherein approximation of the first and second shaft members urges a protrusion extending from the other of the first or second shaft members into the lockout bar to thereby urge the lockout bar from the locked position to the unlocked position.

10. The surgical instrument according to claim 1, wherein the lockout bar is coupled to a rotatable member at a proximal end portion thereof, the rotatable member rotatably coupled to one of the first or second shaft members and configured such that rotation of the rotatable member between a first position and a second position moves the lockout bar between the locked position and the unlocked position.

11. The surgical instrument according to claim 1, wherein each of the first and second jaw members defines a stepped configuration including an interior corner and wherein, yawing of the first and second jaw members from the closed position to the cutting position shears the interior corners relative to one another to cut tissue disposed therebetween.

12. The surgical instrument according to claim 11, wherein the interior corners are chamfered at angles from about 70 degrees to about 80 degrees.

13. The surgical instrument according to claim 11, wherein the interior corners are chamfered at angles of about 75 degrees.

14. The surgical instrument according to claim 1, wherein the handles of the first and second shaft members define finger holes and include annular ramped portions extending about a portion of the circumference of the finger holes, the annular ramped portions configured to facilitate yawing of the handles of the first and second shaft members.

15. The surgical instrument according to claim 1, wherein at least one of the first or second jaw members is adapted to connect to a source of energy for treating tissue grasped between the first and second jaw members, and wherein the lockout bar is moved from the locked position to the unlocked position upon initiation of the supply of energy to the at least one of the first or second jaw members.

* * * * *